United States Patent [19]

Ecanow

[11] Patent Number: 4,914,084
[45] Date of Patent: Apr. 3, 1990

[54] COMPOSITION AND METHOD FOR INTRODUCING HEME, HEMOPROTEINS, AND/OR HEME-HEMOPROTEIN COMPLEXES INTO THE BODY

[75] Inventor: Bernard Ecanow, Wilmette, Ill.

[73] Assignee: Synthetic Blood Corporation, Deerfield, Ill.

[21] Appl. No.: 31,237

[22] Filed: Mar. 26, 1987

Related U.S. Application Data

[63] Continuation-in-part of Ser. No. 1,814, Jan. 8, 1987, Pat. No. 4,794,000, which is a continuation-in-part of Ser. No. 896,844, Aug. 14, 1986, which is a continuation-in-part of Ser. No. 710,648, Mar. 11, 1986, abandoned, Ser. No. 711,066, Mar. 12, 1986, abandoned, and Ser. No. 608,483, May 9, 1984, abandoned.

[51] Int. Cl.$^4$ .................... A61K 37/14; A61K 9/48
[52] U.S. Cl. .................... 514/6; 514/78; 514/410; 514/774; 514/776; 514/814; 424/484; 424/485; 424/491; 424/492; 424/646
[58] Field of Search ............ 514/6, 78, 774, 776, 514/410, 814; 424/484, 485, 491, 492, 147

[56] References Cited

U.S. PATENT DOCUMENTS

| | | | |
|---|---|---|---|
| 4,343,797 | 8/1982 | Ecanow | 514/2 |
| 4,389,331 | 6/1983 | Samejima et al. | 427/213.3 |
| 4,439,424 | 3/1984 | Ecanow et al. | 514/2 |
| 4,539,204 | 9/1985 | Ecanow et al. | 514/6 |
| 4,547,490 | 10/1985 | Ecanow et al. | 514/21 |
| 4,558,032 | 12/1985 | Ecanow et al. | 514/2 |
| 4,596,788 | 6/1986 | Ecanow et al. | 514/2 |
| 4,614,730 | 9/1986 | Hansen | 514/3 |

FOREIGN PATENT DOCUMENTS

| | | | |
|---|---|---|---|
| 130160 | 1/1985 | European Pat. Off. | |
| 1249219 | 1/1966 | Fed. Rep. of Germany . | |
| 2017356 | 1/1972 | Fed. Rep. of Germany . | |
| 2046290 | 1/1972 | Fed. Rep. of Germany . | |
| 2207440 | 1/1973 | Fed. Rep. of Germany . | |
| 2532147 | 6/1981 | Fed. Rep. of Germany . | |
| 3016189 | 10/1981 | Fed. Rep. of Germany . | |
| 2570604 | 3/1986 | France . | |
| 71128 | 7/1974 | Japan . | |
| 80685 | 7/1976 | Japan . | |
| 17328 | 2/1980 | Japan . | |
| 154915 | 12/1980 | Japan . | |
| 79255 | 6/1981 | Japan . | |
| 36633 | 3/1983 | Japan . | |
| 20209 | 2/1984 | Japan . | |
| 21334 | 2/1984 | Japan . | |
| 48923 | 3/1985 | Japan . | |
| 87843 | 5/1985 | Japan . | |
| 126016 | 6/1986 | Japan . | |
| 7311319 | 3/1973 | Netherlands . | |
| 7402359 | 8/1974 | Netherlands . | |
| 8102834 | 10/1981 | PCT Int'l Appl. | 514/814 |
| 558676 | 6/1977 | U.S.S.R. . | |

OTHER PUBLICATIONS

Tsuchida et al, cited in Chem. Abstracts vol. 96:163339p, 1982.
Tsuchida et al, cited in Chem. Abstracts vol. 103:128864x, 1985.
Chaillot et al, cited in Chem. Abstracts vol. 104:17327a, 1986.
Kando, Techniques of Microencapsulation (abstract) Gyogyszereszet 19:401–407 (11) 1975.

*Primary Examiner*—Jacqueline M. Stone
*Attorney, Agent, or Firm*—Marshall, O'Toole, Gerstein, Murray & Bicknell

[57] ABSTRACT

A liquid coacervate composition and a method of introducing heme, hemoproteins and/or heme-hemoprotein complexes into the body. The liquid composition, comprising an oxygen-carrying molecule containing iron and a two-phase aqueous coacervate system, can be administered orally or intravenously. The liquid composition is utilized to augment the oxygen transport capability of the body, to treat for several of the anemias and/or to act as an oxygen-carrying plasma volume extender.

6 Claims, No Drawings

000# COMPOSITION AND METHOD FOR INTRODUCING HEME, HEMOPROTEINS, AND/OR HEME-HEMOPROTEIN COMPLEXES INTO THE BODY

CROSS REFERENCE TO RELATED APPLICATION

This application is a continuation-in-part of Ser. No. 1,814 filed Jan. 8, 1987 now U.S. Pat. No. 4,794,050 which is a continuation-in-part of Ser. No. 896,844 filed Aug. 14, 1986 which is a continuation-in-part of Serial Nos. 710,048 filed Mar. 11, 1986, now abandoned, 711,066 filed Mar. 12, 1986, and 608,483 filed May 9, 1984, now abandoned.

BACKGROUND OF THE INVENTION

1. Field of the Invention

The present invention relates to a liquid composition and a method of introducing heme, and/or hemoproteins, and/or heme-hemoprotein complexes into the body. More particularly, incorporating heme, hemoprotein or a heme-hemoprotein complex into a liquid coacervate system, provides a composition that unexpectedly overcomes the intrinsic instability of heme and therefore is useful in augmenting the oxygen transport capacity of the body; serves as an agent in the treatment of several anemias; and acts as an oxygen-carrying plasma volume expander.

2. Brief Description of the Prior Art

Heme is known to be an unstable molecule However, the incorporation of heme and/or hemoprotein into the coacervate system of the present invention not only unexpectedly improves the stability of heme but also surprisingly provides a composition that is useful in treating blood loss, iron deficiency anemias and for providing oxygen to the body.

The molecular structure of heme, the role of heme in the production of hemoglobin and the physiology of heme are well known. The use of heme and the heme-hemoprotein complex in accordance with the present invention is not taught by the prior art of known blood substitutes using hemoglobin. In the hemoglobin molecule, the protein globulin provides the heme certain physical-chemical properties that increases the stability of heme. Globulin also facilitates oxygen binding and release, and is involved in antigen-antibody reactions.

In the present invention, rather than globulin, the liquid coacervate system, and particularly the surfactants contained therein, is used to stabilize the heme and/or hemoprotein. In addition, the liquid coacervate system composition of the present invention avoids the antigen-antibody reactions associated with hemoglobin, thereby reducing or eliminating the possibility of toxic reactions. The prior art does not teach a composition comprising either heme, a hemoprotein or a complex consisting of heme and a hemoprotein in a two-phase liquid coacervate system.

Blood substitutes based upon a two-phase liquid coacervate system and stroma-free hemoglobin have been prepared previously. However, the present invention, also based upon a coacervate system, utilizes heme, and/or hemoprotein and/or a heme-hemoprotein complex instead of the stroma-free hemoglobin used in the prior art. In accordance with an important feature of the present invention, the molecular structure of heme is identical in all mammals, thereby assuring a virtually unlimited, inexpensive supply of heme. In contrast, the supply of human hemoglobin is limited and expensive and is acceptable for human use only after extensive and costly processing. Therefore, the use of heme, and/or hemoprotein and/or a heme-hemoprotein complex produces non-toxic, effective, and economical compositions compared to presently used products containing stroma-free hemoglobin.

The disclosures of the following Ecanow and Ecanow et al. patents and patent applications are hereby incorporated into this specification by reference.

The Ecanow U.S. Pat. No. 4,343,797 discloses an intravenous synthetic blood substitute comprising a two-phase heterogeneous coacervate system and stroma-free hemoglobin.

The Ecanow et al. U.S. Pat. No. 4,439,424 discloses intravenous synthetic whole blood products in the form of coacervate systems, containing a coacervate phase, an equilibrium bulk water phase and stroma-free hemoglobin.

The Ecanow et al. U.S. patent application Ser. No. 512,917, filed July 12, 1983, now U.S. Pat. No. 4,547,490 discloses a composition wherein a coacervate system is produced from lecithin dispersed in an aqueous solution containing sodium chloride and albumin, then stroma-free hemoglobin and a non-polar or semi-polar solvent, such as n-butyl alcohol, is added to the coacervate system.

The Ecanow et al. U.S. patent application Ser. No. 811,675, filed Dec. 20, 1985, now U.S. Pat. No. 4,738,952 discloses a synthetic whole blood wherein the coacervate system is produced from lecithin dispersed in an aqueous solution containing albumin and sodium chloride. The coacervate system disclosed provides for more effective use of the pyridoxylated-polymerized hemoglobin component of the composition.

The Ecanow U.S. Pat. No. 4,539,204 describes a synthetic blood substitute based on stroma-free hemoglobin and on a coacervate system comprised of two gelatins having different isoelectric points.

The Ecanow U.S. Pat. No. 4,596,788 discloses a synthetic whole blood based upon a coacervate system including gelatin, lecithin, and stroma-free hemoglobin.

The Ecanow U.S. patent application Ser. No. 835,550, filed Mar. 3, 1986,discloses an oral dosage form of insulin based on the use of a coacervate system comprised of lecithin, albumin, and insulin.

The Ecanow U.S. patent application Ser. No. 711,066,now abandoned, filed Mar. 12, 1985, discloses an oral dosage form of atrial peptides, and peptides in general, based on a coacervate including lecithin, albumin, and atrial peptides.

The prior art further includes a publication by Hasegawa describing a blood substitute comprising an amphiphilic heme embedded in a liposome preparation: Hasegawa, E., et al. "Synthesis of Polymeric Liposome Embedded Heme (PLH) and its Possibility as New Synthetic Oxygen Carrier", *J. Pharmacobiodynamics,* 9, No. 9, 117, 1986. However, the composition described by Hasegawa differs from the composition of the present invention in several significant respects. Hasegawa uses a liposome to encapsulate the heme molecule, in contrast to the present invention teaching the use of a coacervate system to incorporate the heme, and/or hemoprotein and/or a heme-hemoprotein complex. This distinction is substantial because in the Hasegawa composition, the heme component is enclosed by lecithin while in the present invention, heme is bound to a surface active agent, such a albumin, as it is in natural blood. In addition, the half-life of heme in liposome systems is significantly shorter than the half-life of heme in coacervate systems.

The liposome vehicle used by Hasegawa and the coacervate system of the present invention are fundamentally different in that the two compositions have different components, possess different properties, and yield different end products.

Generally, the differences between liposomes of Hasegawa and the coacervate system disclosed in the present invention may be summarized as follow:

1. When components such as heme, stroma-free hemoglobin, or drugs are incorporated in the coacervate phase of the coacervate system, a true solution of a transparent, homogeneous, monomolecular dispersion results. The components are truly solubilized and cannot be filtered from the solution. Similar components added to liposomes yield a heterogeneous dispersion of liposomes in a liquid vehicle. These dispersions are not true solutions, such that liposomes, containing the added component, are suspended in a liquid vehicle and the liposomes can be separated from the liquid vehicle.

2. Coacervate systems can be made from a wide variety of surface active agents, whereas true liposomes can be made only from lecithin. According to the method of the present invention, coacervate systems were prepared by using surfactants such as phospholipids, proteins, gums, synthetic polymers, polysaccharides, other natural and synthetic substances rendered surface active by chemical or physical means, and combinations thereof. If a component other than lecithin is used in an attempt to produce a liposome, an encapsulated composition, not a liposome, will result. In such instances, the encapsulating film is not a coacervate-based film.

3. The preparation methods used for coacervate systems and for liposomes are different. For coacervate systems, the specific surfactant and other system components are combined such that a two-phase, liquid, aqueous system results. The physiologically active molecule is typically incorporated into the coacervate phase of the system as a process step in the production of the finished product. Liposomes, however, are made by preparing a film of lecithin and collapsing this film around the physiologically active molecule of the composition.

4. When a particular component is added into the coacervate phase of a coacervate system, the exact quantity and location of the component is known. Therefore, it is possible to precisely formulate and determine the efficacy of the final product. In contrast, with liposomes, it is impossible to accurately determine the quantity and location of any added component. The precise quantity of the physiologically active molecule that adheres to the external surface or to the internal surfaces of the liposome cannot be determined. Furthermore, whenever a physiologically-active molecule having toxic potential has been incorporated in liposomes, the end-use compositions have been associated with toxicity. It has been theorized that either a toxic composition was present on the surface of the liposome or that leakage from the molecule had occurred.

5. The method of manufacture of liposomes and coacervate systems are different. The preparation of a coacervate system using lecithin as a component requires relatively precise adjustment of all component concentrations and conditions, or else two-phase systems either cannot be made or can be made only with great difficulty. For liposome manufacture, precise adjustments are not necessary, because simply placing about 30% to about 50% w/v of lecithin in water will spontaneously produce a liposome.

6. The stability of coacervate systems and the components added into the coacervate system is significantly greater than that of components added to liposomes. It is known that upon introduction into the body, and particularly into the circulatory system, liposomes are unstable and quickly lose their structural integrity. Therefore, because the heme molecule is also known to be very unstable, the use of an unstable liposome vehicle to incorporate unstable heme poses a variety of difficult problems.

From the foregoing facts, the composition and method of the present invention not only differs significantly from the composition described by Hasegawa, but also demonstrates a surprising and unexpected improvement over the teachings of Hasegawa.

The Kokoku Patent No. Sho. 42(1967) 117 discloses the use of a gelatin-based coacervate that incorporates hemoglobin. This Japanese reference describes particles that are approximately the size of erythrocytes (about 7 microns) and that are hardened through the use of formalin. The hardening process fixes the size and rigidity of the particles, and also results in the permanent loss of the coacervate structure. The rigidity of the particles is sufficient to prevent particle deformation that, when combined with the excessive particle size, precludes entrance of the particle into the microcirculation of the patient. In addition, it is known that particles of the size disclosed in the Japanese reference are incompatible with the reticuloendothelial system. Overall, the composition disclosed in the Japanese patent possesses an irreversible toxic characteristic. In contrast, according to the composition and method of the present invention, the coacervate structure of the composition is preserved, thereby providing microencapsulated particles that are, or are capable of distortion to, about 1 micron or less in diameter, can be prepared having substantially larger particle size to undergo distortion without loss of integrity, and are compatible with the microcirculation and the reticuloendothelial system. In addition, microencapsulated particles, of approximately 1 micron or less in diameter, are readily absorbed by the walls of the small intestine, thereby permitting oral administration of the composition. It is theorized that the microencapsulated particles of coacervated material adhere to the membrane of the gastrointestinal tract, thereby facilitating passage of the composition through the small intestine and into the circulatory system.

OBJECTS OF THE INVENTION

It is an object of the present invention to provide a liquid coacervate-based composition, and a method of introducing heme or a heme-hemoprotein complex into the body. It is a further object of the present invention to provide an aqueous coacervate-based composition, incorporating heme or a heme-hemoprotein complex, that can be used to increase the oxygen-transport and iron-transport capabilities of the body, to treat various anemias and/or to extend plasma volume. Other objects will become apparent from the details of the following disclosure.

GENERAL DESCRIPTION OF THE INVENTION

The present invention is directed to a composition including an oxygen-carrying molecule, such as heme, and/or a hemoprotein and/or a heme-hemoprotein complex, incorporated into a two-phase non-toxic, liquid, aqueous coacervate system. The coacervate system formed from a physiologically-active compound together with one or more surfactants and water, serves as a vehicle for the heme, the hemoprotein and/or the heme-hemoprotein complex, the physiologically-active component(s) of the composition of the present invention.

Coacervate systems are formed through a process known as coacervation, said process being the judicious addition of electrolytes, the use of process conditions causing precipitation, such as heat and/or the addition of a precipitating agent such as an alcohol, e.g. n-butyl alcohol, into a colloid solution, resulting in the solution separating into two or more phases or layers. In this invention, the solution separates into two phases (layers). Phase is defined to mean a homogeneous, physically distinct and mechanically separable quantity of matter present in a non-homogeneous physical-chemical system.

In the coacervate system of the present invention, both phases are aqueous. One phase, referred to as the colloid-rich phase, is semi-polar to non-polar in character and is capable of solubilizing oil-soluble and various other water-insoluble compositions of matter. The other phase, referred to as the colloid-poor phase, is polar to semi-polar in character and is capable of solubilizing water-soluble compositions of matter. The polar phase of a coacervate system is one made up of strong dipolar molecules having hydrogen bonding, with dipole moments generally in the range from about 0.8D to about 1.85D. The semi-polar phase is made up of strong dipolar molecules which do not form hydrogen bonds, with dipole moments generally in the range from about 0.1D to about 0.8D. The non-polar phase is made up of molecules having little or no dipole character, generally in the range from 0 to 0.1D. See Remington's Pharmaceutical Sciences, Mack Publishing Co., 1973, pp. 241–242. However, to a limited degree, the colloid-poor phase can solubilize some apparently water-insoluble compounds.

The components comprising the two-phase coacervate system are present in both the colloid-rich and colloid-poor phases; however, the colloid-rich phase has a greater concentration of the components than the colloid-poor phase. The colloid-rich and colloid-poor phases are in equilibrium with each other and immiscible in each other. In addition, the water content of the colloid-rich phase of the coacervate of the present invention is "structured" in a different form than the bulk water of the colloid-poor phase, such that the colloid-poor phase is non-polar The fact that water can have a number of different structures is known to those skilled in the art. Surfactants that can be used to manufacture a coacervate for use in the present invention include anionic, cationic, amphoteric, and non-ionic surfactants. In particular, surfactants especially useful in the composition and method of the present invention include the polysaccarides and their derivatives, mucopolysaccarides; polysorbates and their derivatives; synthetic polymers; pectin; proteins, such as albumin; glycoproteins; glycolipids; phospholipids, such as cephalin, isolecithin, phosphatidyl serum, phosphatidic acid, phosphatidyl choline, phosphatidyl inositol, sphingomyelin, and lecithin; modified fluid gelatin, and mixtures thereof. These surfactants are present in an amount of from about 0.1% w/v to the point of saturation in water.

In addition, components that are not intrinsically surface active also can be used to prepare coacervates useful in the present invention, provided the component can be made surface active by chemical or other modification. For example, fatty acids, generally not considered to be surface active compounds, can be reacted with a suitable alkaline chemical to produce a component having surface active properties. For example, mixing stearic acid with sodium hydroxide will produce a salt of stearic acid, sodium stearate, that possesses strong surface active properties.

Although mixtures of the above-listed surfactants, such as albumin and lecithin, casein and lecithin, gelatin and lecithin, and gelatin and gelatin, generally are preferred in the composition and method of the present invention, coacervate systems also can be made by utilizing a single surfactant, such as albumin or lecithin.

The preferred surfactants for use in the composition and method of the present invention include a mixture of a protein, such as albumin, and a phospholipid, such as lecithin. However, other acceptable coacervate systems have been made using albumin alone, a mixture of two gelatins, lecithin alone, gelatin and lecithin, albumin and pectin, polyethylene glycol and dextran, and casein and lecithin. Similarly, other non-toxic surfactants, either singly or in combination, can be used to prepare a coacervate useful in the present invention.

In accordance with an important embodiment of the present invention, a two-phase, completely aqueous-based coacervate composition is utilized to manufacture the microemulsion of the finished end-product, as distinguished from the two-phase microemulsions that are comprised of a lipid, or oil, phase and a water phase.

According to the method and composition of the present invention any non-toxic molecule capable of carrying, and releasing oxygen to the bloodstream of a patient, preferably a molecule that contains iron, can be used as the physiologically-active component of the composition. Further, it has been found that, in order to achieve the full advantage of the present invention, a heme, and/or a hemoprotein and/or a heme-hemoprotein complex can be used as the physiologically-active component. Since the heme, hemoprotein and heme-hemoprotein complexes contain iron, these preferred compounds possess an important advantage because sources for the physiologically-active component include endogenous, exogenous and synthetic compositions.

As used above and hereinafter, heme is defined to comprise the prosthetic group of hemoglobin. However, according to the composition and method of the present invention, prosthetic groups of other compositions, such as myoglobins, catalases, cytochromes b and some peroxidases can also can be used to form the heme-hemoprotein complexes. The preferred heme molecule for use in the present invention is a complex of iron and protoporphyrin 9, type III. Similarly, hemoproteins that can be used above or in the heme-hemoprotein complex include hemoglobin, ovoglobulin, ovoconalbumin, Cytochrome c, Cytochrome $P_{450}$, polymerized hemoglobin, pyridoxilated-polymerized hemoglobin, ovomucin and lactalbumin. To achieve the full advantage of the present invention, when using a hemoprotein or the heme-hemoprotein complex combination, hemoglobin of human, bovine, synthetic or genetic engineering sources, in stroma-free form, is utilized as the hemoprotein.

In accordance with an important embodiment of the present invention, all of the components of the present invention, and especially the heme, the hemoprotein and/or the heme-hemoprotein complex should be pure and stable. Therefore, either prior to or after incorporating the heme, hemoprotein and/or heme-hemoprotein complex into the composition of the present invention, a solution of the heme, hemoprotein and/or the heme-hemoprotein complex is treated with a chemical agent that forms stable iron complexes with the heme, hemoprotein or heme-hemoprotein complex, such as a carbon monoxide or an inorganic cyanide, particularly cyanide salts or cyanide complexes, such as sodium cyanide hydrogen cyanide. The chemical agent can be removed readily from the heme, hemoprotein and/or heme-hemoprotein complex when an excess of oxygen is introduced into the solution. For example, carbon monoxide is bubbled through the heme, hemoprotein and/heme-protein solution until all oxygen is removed from the solution. In a subsequent processing step, the complexed carbon monoxide is removed by introducing an excess of oxygen to the heme, hemoprotein and/or heme-hemoprotein complex. In accordance with a new and unexpected feature of the present invention, the intimate contact of the solution with carbon monoxide stabilizes the heme, hemoprotein and/or heme-hemoprotein complex during the manufacturing process, thereby preventing oxidation of the heme, hemoprotein and/or heme-hemoprotein complex.

Further, the composition prepared according to the method of the present invention provides iron that is absorbed into the body of humans and other mammals from both the heme, hemoprotein and/or the heme-hemoprotein molecules as intact heme molecules. This absorption duplicates the natural source and natural mode of iron absorption and, therefore, provides a significant improvement over iron compounds now in commercial use. For example, usually the iron that is present in such commercial compositions first must be converted to ferrous iron in the stomach and duodenum before any absorption occurs.

In accordance with an important feature of the present invention, the heme, hemoprotein and/or heme-hemoprotein complex present in the composition after oral administration is protected from degradation in the digestive tract by the coacervate phase of the coacervate system. A film of coacervate-phase water surrounds and completely coats each heme, hemoprotein and/or heme-hemoprotein complex to protect the heme, hemoprotein and/or heme-hemoprotein complex from gastrointestinal degradation. The coacervate-phase water differs in physical structure from the bulk water which is present in the stomach, thereby slowing the diffusion of digestive enzymes in the bulk water. Accordingly, the digestive enzymes are unable to penetrate the film of coacervate-phase water that covers each heme, hemoprotein and/or heme-hemoprotein complex molecule, thereby reducing the rate of interaction of the enzymes with the heme, hemoprotein and/or heme-hemoprotein complex. This slow rate of interaction allows physiologically useful quantities of heme, hemoprotein and/or heme-hemoprotein complex to avoid degradation and, therefore, to pass through the walls of the small intestine and into the circulatory system of the recipient. The protective feature afforded by the coacervate phase also operates to protect the oxygen-carrying physiologically-active component(s) against degradation effects of pH, acid-base balance and other conditions and processes of the gastro-intestinal tract.

In addition, the physiologically active component(s) of the present invention can be incorporated in liposomes or any other non-toxic vehicle, if the liposome or other non-toxic vehicle is then further incorporated into the aqueous coacervate system described herein.

It is desirable to include an enzyme or other chemical as an antioxidant when manufacturing the composition of the present invention. The addition of an antioxidant prevents oxidation of the composition, and stops the generation of free radicals. These free radicals are known to be associated with tissue damage and have adverse physiological effects. Anti-oxidants such as ascorbic acid, sodium ascorbate, atocopherol, other tocopherols or combinations thereof in an amount of at least about 0.1 gram per 100 ml of solution, e.g., from approximately 0.1 g to approximately 20 g per 100 ml of solution, are added to the solution containing heme, hemoprotein and/or heme-hemoprotein before the emulsion step. Excess anti-oxidant does not significantly affect the composition of the present invention so that there is no upper limit to the amount of antioxidant in the composition of the present invention.

The composition of the present invention can be administered orally or intravenously. In addition, the composition of the present invention can be lyophilized using conventional techniques to convert the liquid to a powder. The powdered product then can be reconstituted using appropriate physiological fluids. For instance, when the reconstituted composition is intended for intravenous use, isotonicity and pH should be adjusted to normal body values before administration.

In preparing the compositions of the present invention, it is preferred that both phases of the two-phase, aqueous coacervate system be used. The compositions of the present invention comprise a microemulsion including coacervate-based microemulsified particles containing the physiologically-active component. The microemulsified particles are manufactured to be of appropriate size, such that the particles are compatible with the microcirculation system and the reticuloendothelial system of the human body and other mammals, and can pass through the walls of the small intestine of humans and other mammals. The compositions of the present invention may, if desired, be processed further to produce compositions having time-release characteristics, such as by microencapsulating the particles to provide a time-release hardened coating on the composition.

DETAILED DESCRIPTION OF THE PREFERRED EMBODIMENT

In accordance with an important feature of the present invention, compositions capable of oral or intravenous administration, can be prepared according to the following method. These compositions contain a physiologically-active component that augments the oxygen-transport capability of the body, is useful in treatment of various anemias, and acts as an oxygen-carrying plasma volume expander. Initially, three aqueous solutions are prepared: an aqueous solution including at least about 0.1%, e.g. 0.1 to 5% w/v of a first non-toxic surfactant, such as albumin; optionally an aqueous solution including at least about 0.1%, e.g. 0.1 to 5% w/v of a second surfactant, such as lecithin; and a aqueous solution containing an oxygen-carrying molecule containing iron, such as heme, a hemoprotein and/or a heme-hemoprotein complex. It is preferred that the hemoprotein of the heme-hemoprotein complex be stroma-free hemoglobin.

In accordance with an important embodiment of the present invention, it has been found that the instability of the physiologically-active iron-containing molecule capable of carrying and releasing oxygen (heme and/or the hemoproteins and/or the heme-hemoprotein complex) can be minimized or substantially completely eliminated by treating a solution (preferably aqueous) containing the iron-containing molecule, prior to coacervation, with a chemical complexing agent capable of forming a stable iron complex, such as carbon monoxide or an inorganic cyanide, particularly cyanide salts or cyanide complexes, such as sodium cyanide or hydrogen cyanide, and thereafter treating the complexed solution, preferably to saturation, with an interactant, capable of interaction with the iron complex, to release the complexing agent from the iron-containing molecule which escapes from the solution in gaseous form. To achieve the full advantage of the present invention, the chemical complexing agent is carbon monoxide and the interactant is oxygen or purified air bubbled through the solution in excess to release the carbon monoxide from the iron-containing molecule and saturate the solution to remove the carbon monoxide from the solution. This process of iron-complexing and then interaction to release the complexing molecule will stabilize the physiologically-active iron-containing solution either before or after admixture or emulsification with the other components of the composition so long as the process is carried out prior to coacervation. To achieve full advantage of the present invention, an antioxidant, such as ascorbic acid, is added to the final composition to prevent oxidation of the final composition.

In general, the amount of heme and/or hemoprotein, and/or heme-hemoprotein complex present in the composition of the present invention is determined by the clinically indicated required dose for the treatment of a particular dysfunction. If the composition is to be used to augment the oxygen-carrying capacity of the recipient, the amount of heme, hemoprotein and/or heme-hemoprotein complex in the composition of the present invention is the amount necessary to restore oxygen transport to normal levels within the time frame of the treatment regimen. However, if the intended use of the composition of the present invention is to treat anemic states, such as those due to blood loss, the quantity of heme, hemoprotein and/or heme-hemoprotein complex is the amount necessary to restore normal hemoglobin levels of between approximately 5% and approximately 14% within the time frame of the treatment regimen. Likewise, if the intended use of the composition of the present invention is to treat iron deficiency states, an exemplary amount of heme, hemoprotein and/or heme-hemoprotein complex is that amount that introduces approximately 100–150 mg of elemental iron per dose.

In accordance with the preferred embodiment, the aqueous albumin, lecithin and heme, hemoprotein and/or heme-hemoprotein complex solutions then are thoroughly admixed. Alternatively, the powdered forms of albumin, lecithin, and the heme, hemoprotein and/or heme-hemoprotein complex can be admixed, then converted into a solution by adding sufficient water such that the amount of albumin and lecithin each equals approximately 3% w/v in the finished composition, and the heme, hemoprotein or heme-hemoprotein equals from about 5% to about 30% w/v in the finished composition. This mixture then is subjected to a physical or chemical precipitating agent. For example, heat, ranging from about 20° to about 70° C., is applied until the mixture "precipitates" to produce an aqueous two-phase coacervate system. Temperatures below about 20° C., or above about 70° C., can be utilized according to the method of the present invention so long as the time of heat treatment causes the solution to precipitate into a two-phase coacervate solution while preventing excessive heat treatment to the extent of denaturing the composition causing loss of the coacervate. Alternatively, rather than heating, a non-toxic alcohol, such as ethyl alcohol, or an appropriate electrolyte, such as sodium chloride, can be added to the mixture to produce an aqueous, two-phase coacervate system. The coacervate system then is emulsified using conventional techniques. The isotonicity and the pH of the emulsion are adjusted to approximate the values found in the human body, approximately 0.9% saline. The pH is adjusted using an acid, such as hydrochloric acid, or an alkaline substance, such as sodium hydroxide. Isotonicity is adjusted through addition of an appropriate electrolyte such as sodium chloride, or water as required.

This emulsion can be used as a composition for the oral or intravenous introduction of iron into the body. However, the optional addition of a sterol, such as cholesterol, added in a sufficient amount, for example from about 1% to about 5% w/v based on the total weight of both phases, provides the composition with a degree of surface hardness thereby improving the composition for use as an orally or intravenously administrable composition.

The emulsion also can be processed further, before isotonicity and pH adjustments are made, by using conventional techniques to produce a microemulsion. The microemulsion includes the coacervate-based microemulsified particles and the heme, and/or hemoprotein and/or the heme-hemoprotein complex, each in a form that is compatible with the recticuloendothelial system and microcirculation systems of the human body and is a size that can be absorbed by the intestines. This microemulsion composition can be administered orally or intravenously.

For oral administration, the microemulsion can be dispensed by any of the conventional oral dosage forms, such as liquid microemulsion or soft capsulation, e.g. a syrup or a capsule containing a liquid. In accordance with another important feature of the present invention, the microemulsion can be processed further using either heat or a cross-linking agent to produce a microencapsulated composition having sustained time-release characteristics. Generally, heat, ranging from 25° C. to 70° C., is preferred, and is applied over varying time periods, such as about 2 sec. to about 150 sec., to convert the microemulsion into microencapsulated particles having varying degrees of surface-coacervate film hardnesses. The microemulsified coacervate can also be treated at temperatures about 70° C., or below 25° C., for a time sufficient to produce a time-release composition capable of releasing the physiologically-active component, for example, up to about 72 hours, after administration of the composition. It has been found that longer heating time increases the film hardness, thereby affecting the time-release characteristics of microencapsulated particles. Therefore, particles of similar or different release rates can be combined in a single dose and can be administered orally or intravenously after being placed in an appropriate vehicle or dosage form.

In accordance with the present invention, coacervate systems also can be produced by using a single surfactant, such as albumin alone, and a precipitating agent. The precipitating agent can be a non-toxic alcohol, such as isopropyl alcohol or n-butyl alcohol, electrolytes, heat, or a combination thereof. Similarly, an alternative coacervate system that can be used in the compositions of the present invention, can be manufactured by preparing an aqueous solution of a surfactant, such as lecithin, and then adding a precipitating agent, such as an alcohol or an electrolyte in sufficient amount for phase separation to yield a coacervate system. Subsequent processing steps for these alternative coacervates to produce orally or intravenously administrable microemulsified or microencapsulated compositions are identical to the processing steps described above.

EXAMPLES

EXAMPLE 1

An aqueous 3% w/v solution of albumin, an aqueous 3% w/v solution of lecithin and an aqueous solution of heme, containing the dose of heme desired in the end product, are thoroughly admixed after the heme solution was treated with sufficient carbon monoxide to drive off essentially all the oxygen. The mixture then is heated at 50° C. for a sufficient time to produce a two-phase coacervate system. The two-phase coacervate system then is emulsified in a blender, followed by the addition of an antioxidant, such as ascorbic acid, and by adjustment of (1) isotonicity using sodium chloride and/or water and (2) pH using either an acid or a base, such as hydrochloric acid or sodium hydroxide in an amount sufficient to bring the isotonicity and pH values of the emulsion within normal physiological ranges, e.g., 7.2 to 7.5 pH. The emulsion then is converted, by conventional colloid mill techniques to a microemulsion of coacervate-based microemulsified particles, having a diameter of approximately 1 micron or less. The composition containing the microemulsified particles, containing encapsulated heme, then is adjusted for isotonicity and pH as above, if necessary. The microemulsified particles can be used for oral or intravenous administration to the body. This microemulsified composition then is heated at 60° C. for about 2 to about 150 seconds to produce hardened, microencapsulated particles having a range of sustained time-release characteristics. The microencapsulated particles then are treated with excess oxygen to remove the carbon monoxide, and, optionally, stored under an inert blanket of nitrogen gas. These hardened, microencapsulated particles, when added to a suitable vehicle, such as syrup, also can be used orally, or in a physiological saline solution intravenously. These compositions are useful to augment the oxygen-transport capacity of the recipient and to increase circulatory volume.

EXAMPLE 2

The procedure of Example 1, except that a complex of heme and stroma-free hemoglobin replaced the heme.

EXAMPLE 3

The procedure of Example 1, except that an aqueous solution of 3% w/v of casein replaced the aqueous 3% w/v solution of albumin.

EXAMPLE 4

The procedure of Example 1, except that an aqueous 3% w/v solution of gelatin replaced the aqueous 3% w/v solution of albumin.

EXAMPLE 5

The procedure of Example 1, however the manufacturing process was terminated after preparation of the coacervate system microemulsion, thereby producing an orally administrable composition useful in the treatment of iron deficiency anemia, and anemias due to blood loss.

EXAMPLE 6

The procedure of Example 5, except that a heme and stroma-free hemoglobin complex replaced the heme, thereby producing a composition useful in treating anemias due to iron deficiency or blood loss.

EXAMPLE 7

The procedure of Example 1, except that the preparation of the microencapsulated sustained time-release formulation is omitted.

EXAMPLE 8

The procedure of Example 1, except that the complex of heme and stroma-free hemoglobin is used, and the manufacturing process is terminated after preparation of the microemulsion.

EXAMPLE 9

The procedure of Example 1, except that an aqueous 5% w/v solution of albumin is used instead of the aqueous 3% w/v albumin solution.

EXAMPLE 10

The procedure of Example 1, except that an aqueous 4% w/v solution of lecithin is used instead of the aqueous 3% w/v lecithin solution.

EXAMPLE 11

The procedure of Example 1, except that the coacervate system is produced by subjecting an aqueous 3% w/v solution of albumin to temperatures of 30°-35° C. until formation of a two-phase coacervate system.

EXAMPLE 12

The procedure of Example 1, except that the coacervate system is prepared by the dropwise addition of ethyl alcohol to to an aqueous 3% w/v solution of lecithin until a two-phase coacervate system is produced

EXAMPLE 13

The procedure of Example 1, except that an aqueous 3% w/v solution of casein is used to replace the aqueous 3% w/v albumin solution, and a complex of heme and stroma-free hemoglobin is used to replace the heme.

EXAMPLE 14

The procedure of Example 1, except the heme molecule is first encapsulated in a lecithin-cased liposome before proceeding to produce the aqueous two-phase coacervate system.

EXAMPLE 15

The procedure of Example 1, except the heme-hemoglobin complex is first encapsulated in a lecithin-cased liposome before proceeding to produce the aqueous two-phase coacervate system.

I claim:

1. A method of stabilizing a solution of an iron-containing molecule capable of carrying and releasing oxygen comprising intimately contact the solution with a chemical agent capable of forming a complex with iron prior to coacervation to complex substantially all of the iron-containing molecules with said chemical agent, in solution, with said chemical agent; thereafter, intimately contacting the solution with an interactant capable of interacting with said chemical agent, as complexed with the iron-containing molecules in solution, to release said chemical agent from solution; and including the iron-containing molecule within a coacervate phase of a two-phase coacervate composition.

2. The method of claim 1 wherein the iron-containing molecule capable of carrying and releasing oxygen is selected from the group consisting of heme, a hemoprotein, and a mixture of heme and a hemoprotein.

3. The method of claim 1 wherein the chemical agent is gaseous carbon monoxide.

4. The method of claim 3 wherein the solution intimately contacted the carbon monoxide by bubbling carbon monoxide through the solution until substantially all of the iron in the iron-containing molecules are complexed with carbon monoxide.

5. The method of claim 1 wherein the interactant comprises oxygen.

6. The method of claim 5 wherein the solution is intimately contacted with oxygen by bubbling oxygen through the solution until substantially all of the complexed carbon monoxide is replaced by oxygen.

* * * * *